United States Patent [19]

Ring et al.

[11] Patent Number: 4,655,758
[45] Date of Patent: Apr. 7, 1987

[54] MICROBIAL POLYSACCHARIDE ARTICLES AND METHODS OF PRODUCTION

[75] Inventors: David F. Ring, Skillman; Wilson Nashed, North Brunswick; Thurman Dow, Somerville, all of N.J.

[73] Assignee: Johnson & Johnson Products, Inc., New Brunswick, N.J.

[21] Appl. No.: 749,914

[22] Filed: Jun. 27, 1985

Related U.S. Application Data

[63] Continuation-in-part of Ser. No. 450,324, Dec. 16, 1982, Pat. No. 4,588,400.

[51] Int. Cl.⁴ .............................................. A61F 13/16
[52] U.S. Cl. .................................... 604/374; 128/156; 428/296; 162/100
[58] Field of Search .............. 604/304, 289, 374, 375, 604/376, 377, 378, 379; 162/100; 128/155, 156; 428/296, 297, 298, 299

[56] References Cited

U.S. PATENT DOCUMENTS

| | | | |
|---|---|---|---|
| 4,474,949 | 10/1984 | Chatterjee et al. | 604/374 X |
| 4,536,432 | 8/1985 | Holtman | 604/374 X |
| 4,588,400 | 5/1986 | Ring et al. | 604/289 X |
| 4,591,501 | 5/1986 | Cioca | 604/304 X |

*Primary Examiner*—John D. Yasko
*Attorney, Agent, or Firm*—Wayne R. Eberhardt

[57] ABSTRACT

Laminar polysaccharide structures, e.g., laminar microbial cellulose structures, are disclosed. These structures comprise densified planiform sheets or laminae that merge into one another and together define plural regions having reduced polysaccharide microfibril density. The disclosed laminar polysaccharide structures are derived by manipulating fibrous polysaccharide pellicles produced by microorganisms such as those of the genere Acetobacter, Rhizobium, Agrobacterium, Pseudomonas, Sphaerotilus, and the like.

23 Claims, 16 Drawing Figures

MICROBIAL POLYSACCHARIDE ARTICLES AND METHODS OF PRODUCTION

CROSS REFERENCE TO RELATED MATERIALS

This application is a continuation-in-part of copending U.S. application Ser. No. 450,324 filed on Dec. 16, 1982 now U.S. Pat. No. 4,588,400.

TECHNICAL FIELD

This invention relates to articles derived from microbial polysaccharides, such as microbial cellulose, and to methods for producing such articles.

BACKGROUND OF THE INVENTION

Polysaccharides such as cellulose are natural biological homopolymers of glucose residues linked in a 1,4-beta configuration. Such glucan chains associate with one another and form useful insoluble threads or strands.

Cellulose is an extremely abundant macromolecule. Estimates for its yearly production range between $10^9$ and $10^{11}$ tons. Because of its abundance and useful physical properties cellulose has been employed as the starting material for a wide variety of articles of manufacture ranging from absorbents, to materials of construction, to fillers for food products.

Cellulose and like polysaccharides are synthesized not only by various plant systems, such as grasses, trees, cotton plants, and the like, but also microorganisms. For commercial uses the plant systems, e.g., trees and cotton plants, are the primary sources of cellulose.

Isolation of cellulose from wood is performed usually by three commercial processes: the sulfite process, the sulfate process, and the soda process. The objective is to separate individual cellulose fibers with minimum mechanical damage as the wood is comminuted or pulped, and to then selectively recover these fibers while leaving behind the other constituents of the wood or other plant material source. Various pulping processes are known.

However, the cellulose recovered from a pulping process is relatively coarse. Also, the recovered fibers are relatively short in length and have relatively large effective diameter. For example, the recovered cellulose fibers are about 0.5 to about 4 millimeters in length, and have a width of about 0.02 to about 0.07 millimeters. However, for many applications fibers of such dimensions are much too coarse.

Cellulosic fibers that are several orders of magnitude finer are produced by microorganisms. While the existence of microbial cellulose has been known for about 100 years, it has remained by and large a laboratory curiosity.

An approach to reduce further the size of pulp is described in U.S. Pat. No. 4,374,702 to Turback, which patent describes a methods for the production of microfibrillated cellulose.

The structure of natural microbial cellulose membranes has been described by Purz et al. in Faserforshung and Textiltechnik 28 (4): 155–163 (1977) and in Faserforschung and Textiltechnik 27 (11): 561–570 (1976), and in West German Pat. Nos. 88,307, 92,136, and 93,100. A process for tanning a naturally grown microbial pellicle is described in U.S. Pat. No. 1,141,545. A method for coating synthetic fibers with microbial cellulose is described in U.S. Pat. No. 4,378,431 to Brown, Jr.

It has now been found that microbial polysaccharide pellicles, e.g., microbial cellulose pellicles, can be transformed from a naturally-occurring entangled fiber mass into laminar structures having enhanced physical properties by controlled physical manipulation of the pellicles.

Summary of the Invention

This invention provides a laminar polysaccharide structure wherein densified planiform sheets or laminae merge into one another and together define plural regions having a reduced polysaccharide microfibril density. A further aspect of this invention contemplates a method for producing the aforementioned laminar structure.

The present laminar structure is self-supporting and is constituted by densified, interconnected planiform sheets or laminae that merge into one another defining channels therebetween. Situated within the defined channels and connected to the laminae that define these channels are polysaccharide microfibrils. The microfibril density within these channels is less than the microfibril density in naturally-occurring pellicles such as pellicles of microbial cellulose. The defined channels and the microfibrils therein provide enhanced liquid transport and/or retention within the structure. Accordingly, the present articles are well suited as absorbent materials and as carriers for various liquid substances.

For the purposes of the present invention, cellulose derived from a microbial source is the preferred polysaccharide.

The laminar structures or webs of the present invention have a wide variety of uses, e.g. as wound dressings and bandages, treatment pads, medicament delivery systems, absorbent pads or mats, packaging and wrapping materials, protective drapes, wipes, and the like.

A particularly useful article of manufacture that can be made from the present polysaccharide laminar structure is a pliant, water absorbent fibrous mass of microbial cellulose that is partially saturated with water and additionally contains a water-miscible, organic liquid lubricant having a vapor pressure of no more than about 24 millimeters of mercury at 25° C. This organic liquid is present in a polysaccharide-to-lubricant weight ratio of about 100 to about 0.007. Particularly suitable lubricants for this purpose are polyhydric alcohols such as glycerol, sorbitol, polyethylene glycol, polypropylene glycol and the like. The pliant mass, when derived from fibrous microbial cellulose, is particularly useful as a wound dressing.

The self-supporting laminar polysaccharide structures of the present invention are prepared by physical manipulation of a polysaccharide pellicle produced by a microorganism. Specifically, a water-containing pellicle, while in a wet state, is reduced one or more times to a thickness of no more than about 25 percent of its original thickness and so as to express at least some of the liquid present, preferably at least about 40 weight percent and more preferably at least about 80 weight percent of the liquid present, and to effect a permanent rearrangement of the polysaccharide strands thereof into a laminar structure. This thickness reduction is effected while providing a pathway for water exit from the pellicle. The thickness reduction can be achieved by compressing the pellicle between porous or foraminous platens, e.g., perforated platens, sponge-lined platens, or the like, by tensioning, or by similar expedients. It has been found that a pellicle so manipulated does not recover to its original thickness upon release of the pressure or tension but, instead, exhibits enhanced desirable physical properties.

BRIEF DESCRIPTION OF THE DRAWINGS

In the drawings.

In the foregoing photomicrographs the left-hand portion of the photomicrograph shows the structure at 200× magnification and the right-hand portion of the photomicrograph shows the structure at 800× magnification. The relatively lighter field in the left-hand portion of each photomicrograph delineates that portion of the structure which is shown at 800× magnification in the right-hand portion of the same photomicrograph.

DESCRIPTION OF PREFERRED EMBODIMENTS

Suitable sources of starting materials for production of the articles of the present invention are fibrous polysaccharide-producing microorganisms, particularly cellulose-producing microorganisms of the genera Acetobacter, Rhizobium, Agrobacterium, Pseudomonas, Sphaerotilus, and the like. See, for example, Brown et al., J. Applied Polymer Science: Appl. Polymer Syrup. (1983) 37:37-38 and U.S. Pat. No. 4,320,198 to Mynatt.

A particularly preferred microorganism for the purposes of the present invention is *Acetobacter xylinum*.

Generally, such microorganisms can be cultivated under quiescent aerobic conditions, with attendant pellicle production, in a suitable acidic nutrient medium, usually at a pH of about 3.5 to about 6.0, at a temperature of about 15° C. to about 35° C., preferably at about 20° C. to about 30° C. One suitable nutrient medium, especially for microorganisms of the genus Acetobacter is the so-called Schramm/Hestrin medium described in Schramm et al., J. General Biology (1954) 11:123–129. This particular medium is constituted by glucose (about 20 g/l), peptone (about 5 g/l), yeast extract (about 5 g/l), anhydrous dibasic sodium phosphate (about 2.7 g/l), and citric acid monohydrate (about 1.15 g/l). The pH value of this particular medium is adjusted to a value of about 3.5 to about 6.0 by the addition of hydrochloric acid.

Also, as has been reported in Nature (1947) 159:64–65, rapid microbial cellulose production has been observed in a culture medium based on fructose, mannitol and sorbitol, as well as in a glucose-containing medium. Relatively slower growth rates have been observed with glycerol, galactose, lactose, sucrose, and maltose.

A nutrient medium for microbial cellulose-producing microorganisms also can be based cellooligosaccharides such as cellobiose as described in Japanese Pat. Disclosure No. 37889-1979 by Yamanaka et al.

To produce the articles of the present invention, a pellicle grown in a nutrient medium is harvested and then treated to remove or express liquid retained therein and to dislocate the polysaccharide, e.g., cellulose, strands that are present in the pellicle as grown to produce a laminar structure. Preferably at least about 40 weight percent of the liquid initially present is expressed, and more preferably at least about 80 weight percent of the liquid initially present is expressed. The initial thickness reduction of the harvested pellicle not only expresses a portion of the liquid contained therein but also rearranges the strand orientation and produces a laminar structure as can be readily seen in the FIGURES.

Liquid expression from the pellicle can be a batch or a continuous process, as desired. In a batch process, a pellicle can be positioned between perforated and/or liquid absorbing platens that compress the pellicle therebetween to the desired degree without rupturing the pellicle. In a continuous process, the pellicle is passed between rotating pairs of foraminous or absorbent rolls or rollers, foraminous or absorbent belts, and the like devices that compress a pellicle segment as it passes through. The rate of liquid expression from the pellicle is controlled so as to avoid rupture of the pellicle while effecting a permanent change in its fiber morphology. Usually the desired amount of liquid can be expressed in about 2 to about 30 seconds.

The liquid expression rate and pressure can vary, depending upon the thickness of the pellicle, and the degree of desired pellicle deformation, degree of lamination and laminar density desired, and like factors. However, in all instances the liquid expression pressure is sufficient to effect a permanent deformation of the fiber morphology which deformation is not restored upon a subsequent immersion in water. In this regard, the pellicle is compressed or tensioned so that upon release of the expression pressure the pellicle thickness will recover to no more than about 75 percent of the original pellicle thickness. Such pellicle deformation is achieved by initially reducing the pellicle thickness to no more than about 25 percent of its original thickness.

Further treatment of the laminar structure produced during the liquid expression step is dictated primarily by the intended end use for the product. For example, if it is desired to cleanse the produced laminar structure from nutrients, pyrogens, cells, and cell debris present after the initial liquid expression step, the laminar structure can be washed with water, aqueous sodium hydroxide solutions, and like substances, and subjected to additional cycles of liquid imbibition and expression. Also, the laminar structure may be boiled in an aqueous alkaline solution for a time period sufficient to remove the cells, cell debris, and other pyrogenic materials that may be present, then washed in a neutralizing solution and in distilled water, and at least subsequently pressed or otherwise deformed to produce a laminar structure or web that is substantially pyrogen free and ash free, and thus is suitable for the manufacture of sterile bandages, or wound dressings, or the like.

Preferably, the present cleaned laminar structure contains no more than about 0.1 percent by weight protein, no more than about 0.00001 percent by weight of endotoxins, no more than about 1 percent by weight ash, and/or no more than about 0.001 percent by weight heavy metal ions. All of the foregoing percentages are based on the weight of polysaccharide present in the structure. Therapeutic substances, such as various types of medication, humectants, disinfectants, antiseptics, analgesics, anesthetics and the like, can be introduced into the cleansed laminar structure by a wide variety of techniques as will be illustrated in detail hereinbelow, for example, by soaking, by direct injection into the laminar structure, by dusting solid medicaments onto the laminar structure, by passing of a fluidized stream of a particulate solid medicament throughout the laminar structure so that a predetermined amount of the particulate medicament becomes physically entrapped therein, etc. Illustrative anesthetics that can be incorporated within the laminar structure are the local anesthetics of the tertiary or secondary amino type such as procaine, cocaine, lidocaine, or the like. Illustrative analgesics that can be incorporated within the laminar structure are the salicyates, e.g., salicylic acid, sodium salicylate, acetylsalicylic acid (aspirin), etc., salicylate congeners, e.g., salicylamide, the para-aminophenol derivatives, e.g., phenacetin, acetaminophen, acetanilid, the pyrazolon derivatives, e.g., antipyrine, aminopyrine, and the like.

Similarly, the laminar structure can be impregnated with an isotonic electrolyte, with a depilatory, with an oxygen-bearing liquid or emulsion, e.g., an aqueous hydrogen peroxide solution, an oxygenated perfluorocarbon emulsion containing a perfluorocarbon described in U.S. Pat. No. 4,289,499 to Clark et al., and similar substances.

Also, the laminar structure can contain a bacterial culture medium, e.g., trypticase broth, mycophil broth, and serve as a convenient means for various bacterial or fungal culture and diagnostic purposes.

A laminar structure cleansed to the desired degree can contain water in an amount of up to about 100 times its weight. Some of this retained water can be removed to produce a moist, pliant but water absorbent article. If, on the other hand, substantially all of the water present in the structure is removed, the laminar structure may or may not be absorbent, depending upon the manner the retained water was removed and the degree of hydrogen bonding that was effected among the polysaccharide strands during water removal.

Water within a laminar structure of the present invention can also be replaced in whole or in part by treatment with a water-miscible, organic liquid fiber lubricant to produce a water-absorbent article that is relatively soft and pliant. To that end, into a partially water-saturated or water-laden, laminar mass derived from a microbial polysaccharide, such as microbial cellulose, is introduced a water-miscible, organic liquid having a vapor pressure at 25° C. no more than that of water, i.e., about 24 mm of Hg at 25° C., to provide a polysaccharide-to-lubricant weight ratio of about 100 to about 0.007. The amount of water present in such a structure can be in the range of about 10,000 to about 30 percent by weight, based on the weight of the microbial polysaccharide present. If desired, the water content may be adjusted in the organic liquid lubricant-treated laminar mass by evaporation or in any other convenient manner.

Liquid lubricants suitable for this purpose, especially for the treatment of microbial cellulose laminar structures, are the polyhydric aliphatic alcohols such as ethylene glycol, propylene glycol, glycerol, pentaerythritol, pinacol and the like, including the sugar alcohols, i.e., alcohols derived from a sugar, such as mannitol, sorbitol, arabitol, xylitol, and the like.

Also suitable are liquid polyethylene glycols of the formula $$H(OCH_2CH_2)_nOH$$

wherein n is an integer having a value of at least 4. Illustrative of such lubricants are polyethylene glycol 200, polyethylene glycol 400, and polyethylene glycol 600.

The aforementioned treatment of a water-containing laminar structure of the present invention results in a pliant, water-absorbent, laminar mass derived from a microbial polysaccharide, such as microbial cellulose, and containing a water-miscible, organic liquid fiber lubricant in an amount of about 100 to about 0.007 weight percent, based on the weight of polysaccharide present.

The present invention is illustrated further by the following examples, which are not to be taken as limiting.

EXAMPLE 1

Preparation of Laminar Polysaccharide Structures

Microbial Growth Conditions & Sample Preparation

Two strains of *A. xylinum* were cultured under the same conditions. The growth medium in each instance was Schramm/Hestrin medium modified by substituting diammonium phosphate for the peptone usually present. Inoculation was at 5% with a standard three-day culture. The growth temperature was 20° C. The duration of growth (fermentation) was seven days.

Five trays of 16" by 20" pellicles were grown with each strain. Thereafter the pellicle from each tray was slit into 5" by 8" labeled pieces that were subjected to different processing techniques and testing procedures.

Processing Conditions

Figure 1:
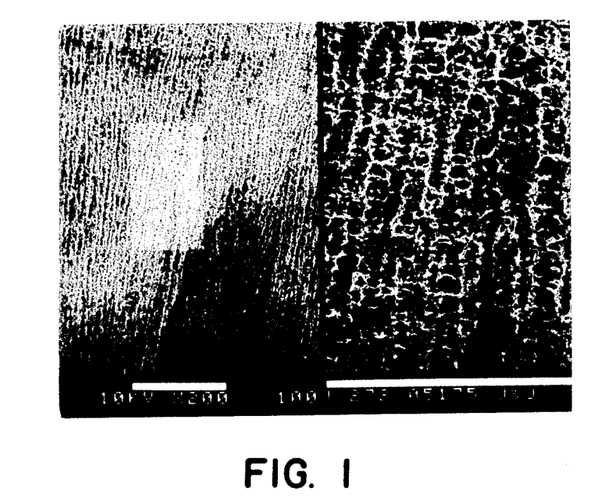
FIG. 1 is a photomicrograph at 200× and 800× magnifications of a cross-section of a microbial cellulose pellicle produced by a species of *Acetobacter xylinum*.
Figure 9:
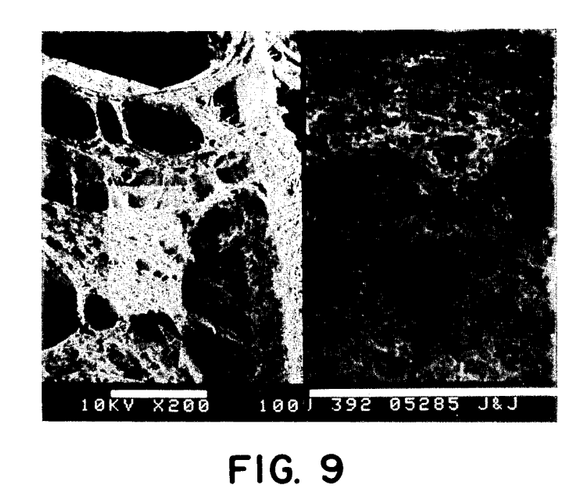
FIG. 9 is a photomicrograph at 200× and 800× magnifications of a cross-section of a microbial cellulose pellicle produced by another species of *A. xylinum*.

The materials shown in FIGS. 1 and 9 were prepared by placing a piece of a harvested pellicle into water (about 1000 cc) and storing it at 4° C. until testing or other use. These materials were never pressed nor permitted to sit out of water under own weight. Pellicle pieces treated in the foregoing manner served as unprocessed standards.

Figure 2:
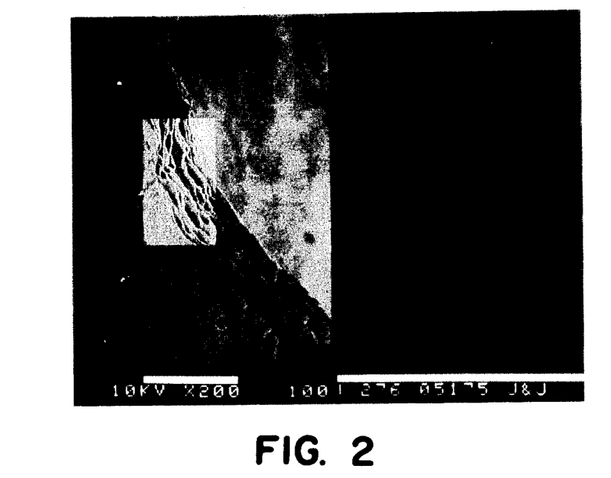
FIG. 2 is a photomicrograph at 200× and 800× magnifications of a cross-section taken from a pellicle produced by the same species as that of FIG. 1 after that pellicle was manipulated in accordance with the present invention by pressing twice to about 98 wt-% liquid removal.
Figure 10:
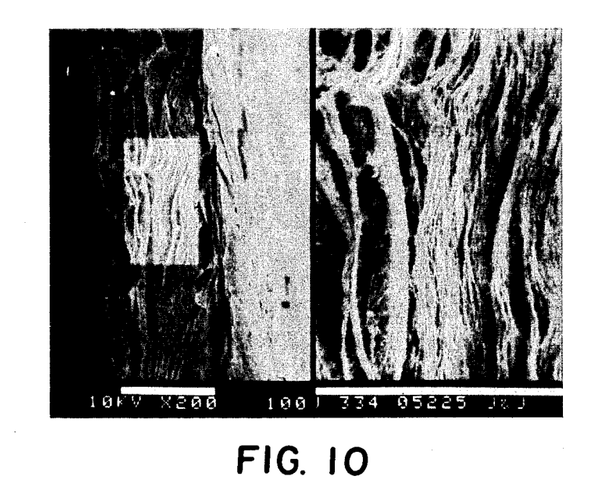
FIG. 10 is a photomicrograph at 200× and 800× magnifications of a cross-section of a pellicle produced by the same species as that of FIG. 9 but pressed twice to about 95 wt-% liquid removal.

The materials shown in FIGS. 2 and 10 were placed in water (about 1000 cc) after harvesting and cutting and then pressed twice at 196 pounds per square inch (psi) while positioned between layers of absorbent toweling that served as liquid accepting surfaces. Pressure was maintained for about 30 seconds and until about 98 wt-% and 95 wt-%, respectively, of the liquid originally present in the material had been removed. After pressing, the obtained materials were stored in an air-tight container at 4° C.

Figure 3:
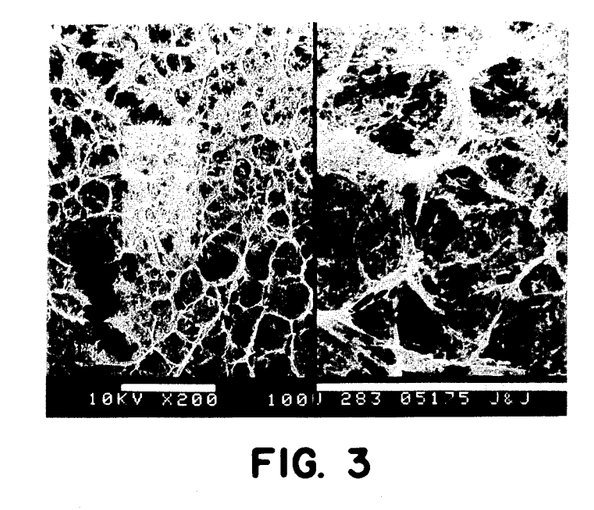
FIG. 3 is a photomicrograph at 200× and 800× magnifications of a cross-section of a pellicle produced by the same species as that of FIG. 1 and treated as that shown in FIG. 2 but after re-expansion by immersion in water.
Figure 11:
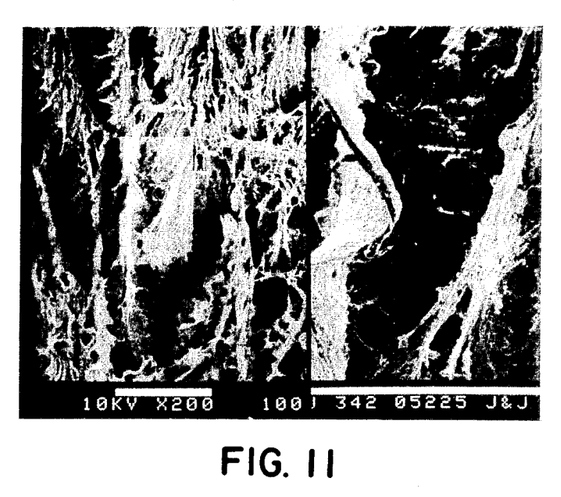
FIG. 11 is a photomicrograph at 200× and 800× magnifications of a cross-section of a pellicle produced by the same species as that of FIG. 9, pressed twice to about 95 wt-% liquid removal, and re-expanded by immersion in water.

The materials shown in FIGS. 3 and 11 were subjected to the same processing as the materials shown in FIGS. 2 and 10, above, except that after pressing but before storage the materials were immersed in excess water at 4° C. for 24 hours and permitted to expand.

Figure 4:
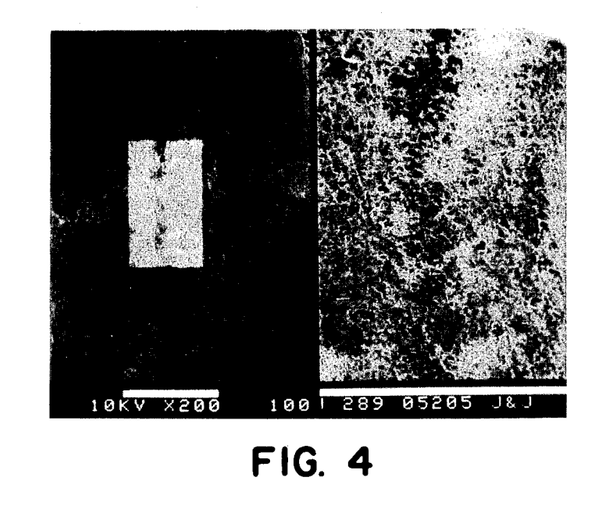
FIG. 4 is a photomicrograph at 200× and 800× magnifications of a cross-section of a pellicle produced by the same species as that of FIG. 1 after boiling in an aqueous 1 wt-% sodium hydroxide solution for one hour and rinsed to neutral pH.
Figure 12:
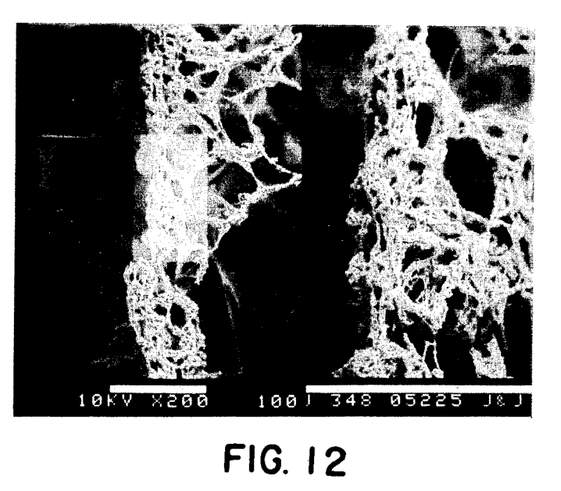
FIG. 12 is a photomicrograph at 200× and 800× magnifications of a cross-section of a pellicle produced by the same species as that of FIG. 9 after boiling in an aqueous 1 wt-% sodium hydroxide solution for one hour and rinsed to neutral pH.

The materials shown in FIGS. 4 and 12, after initial storage in water (1000 cc at 4° C.) were transferred to a 1 wt-% aqueous NaOH solution (2000 cc) and boiled for one hour. Thereafter the materials were rinsed once with an aqueous acetic acid solution and then repeatedly with water until rinse water having a pH value of 7 was obtained. Twelve water rinses were used to reach pH 7.

Figure 5:
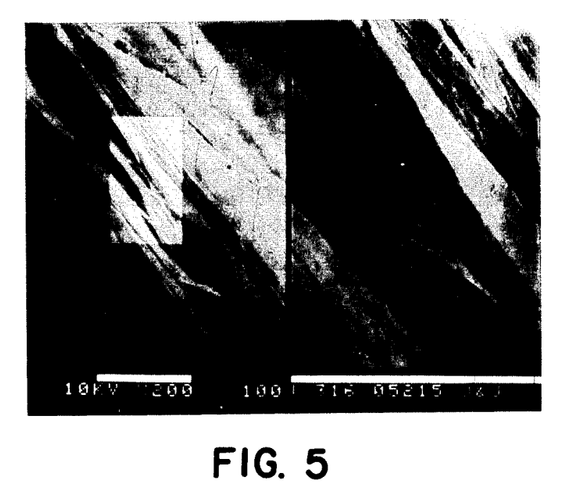
FIG. 5 is a photomicrograph at 200× and 800× magnifications of a cross-section from a pellicle derived from the same species as in FIG. 1, pressed to 91 wt-% water removal, and thereafter boiled in an aqueous 2 wt-% sodium hydroxide solution for three one-hour periods with pressing after each boiling period and repeated washing and pressing after the boiling periods.
Figure 13:
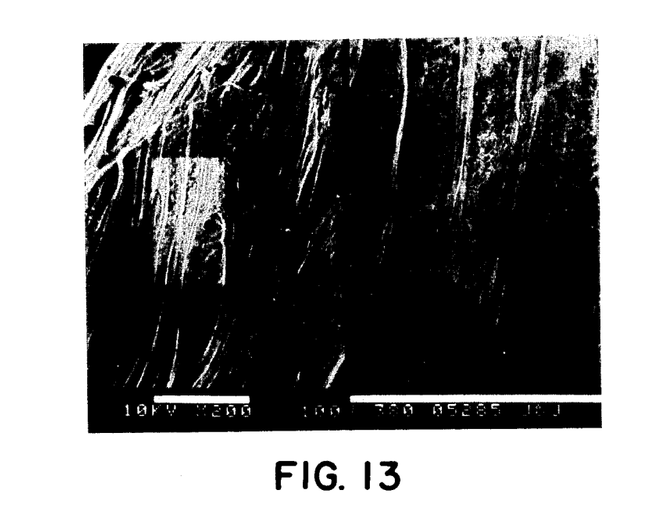
FIG. 13 is a photomicrograph at 200× and 800× magnifications of a cross-section of pellicle derived from the same species as in FIG. 9, treated in the same manner as the pellicle of FIG. 5 except pressed to about 85 wt-% liquid removal.

The materials shown in FIGS. 5 and 13, after initial storage in water (1000 cc at 4° C.), were pressed at 196 psi for about 30 seconds while positioned between layers of polyurethane foam. For the material shown in FIG. 5, pressing was continued until 91 wt-% of the liquid originally present was removed. The material shown in FIG. 13 was pressed until 85 wt-% of the liquid originally present was removed. The pressed materials were thereafter placed in a boiling 2 wt-% aqueous NaOH solution and boiled for one hour. The materials were then pressed as above to 91 wt-% and 85 wt-% liquid removal, respectively. The boiling and pressing steps were repeated two more times. These three boiling and pressing cycles were followed by eight water rinses, each of at least one-hour duration, to a pH value of 7. Each of the water rinses was followed by a pressing step carried out as described above. After the final pressing step the materials were stored in an air-tight container at 4° C.

Figure 6:
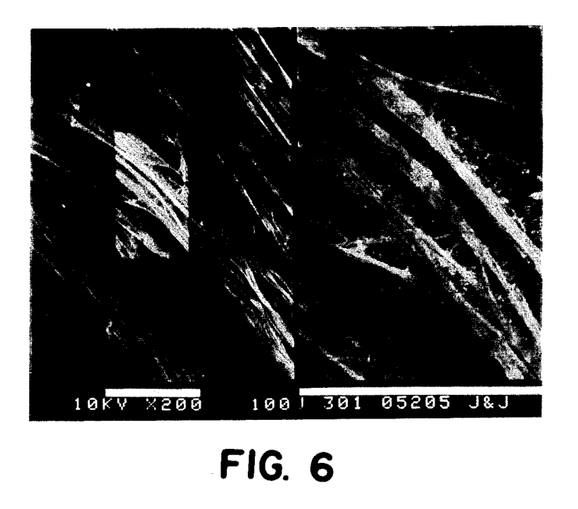
FIG. 6 is a photomicrograph at 200× and 800× magnifications of a cross-section from a pellicle derived from the same species as in FIG. 1, pressed to 91 wt-% water removal, thereafter boiled in an aqueous 2 wt-% sodium hydroxide solution for three one-hour periods with pressing after each boiling period, repeatedly washed and pressed after the boiling periods, and then re-expanded by immersion in water.
Figure 14:
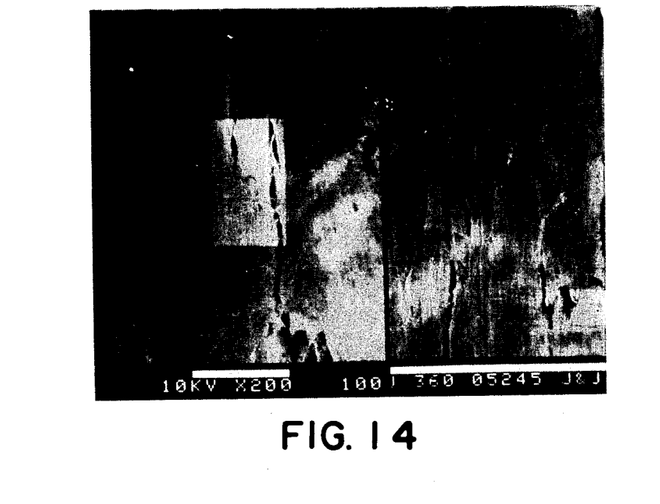
FIG. 14 is a photomicrograph at 200× and 800× magnifications of a cross-section of a pellicle derived from the same species as in FIG. 9, treated in the same manner as the pellicle of FIG. 6 except pressed to about 85 wt-% liquid removal.

The materials shown in FIGS. 6 and 14 were treated in the same manner as the materials shown in FIGS. 5 and 13, above, except that the materials were immersed into excess water at 4° C. for twenty-four hours after the final pressing step but before storage.

Figure 7:
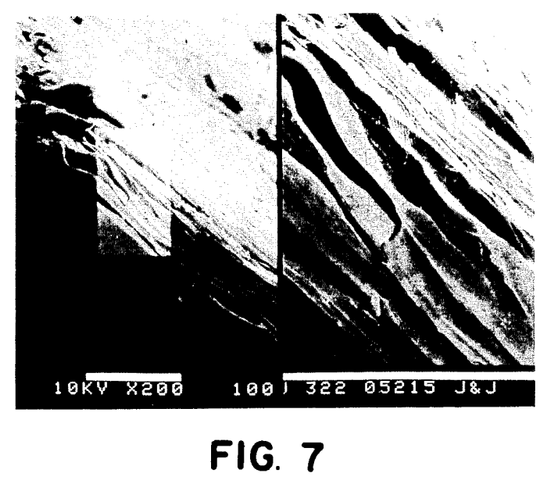
FIG. 7 is a photomicrograph at 200× and 800× magnifications of a cross-section from an *A. xylinum* pellicle derived from the same species as in FIG. 1, pressed first to a 91 wt-% liquid removal, thereafter boiled in an aqueous 2 wt-% sodium hydroxide solution for three one-hour periods with pressing after each boiling period, repeated washing and pressing after the boiling periods, and finally pressed to a 98 wt-% liquid removal.
Figure 15:
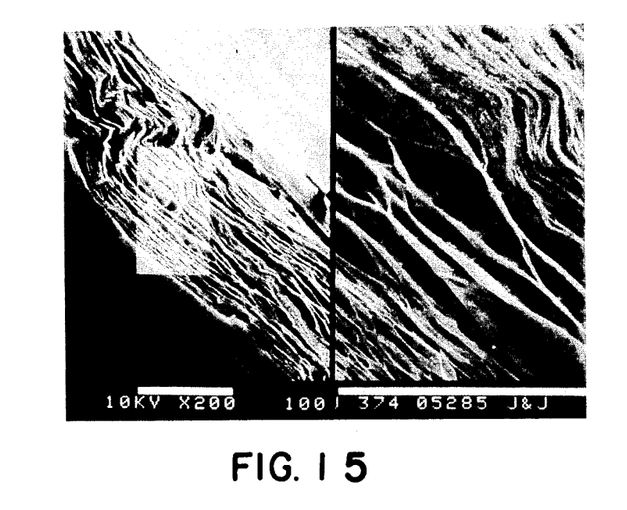
FIG. 15 is a photomicrograph at 200× and 800× magnifications of a cross-section of a pellicle derived from the same species as in FIG. 9, treated in the same manner as the pellicle of FIG. 7 except first pressed to about 85 wt-% liquid removal and finally to about 95 wt-% liquid removal.

The materials shown in FIGS. 7 and 15 were processed in the same manner as the materials shown in FIGS. 5 and 13, above, except the final pressing step was done between layers of absorbent toweling and pressure was maintained on the material until 98 wt-% and 95 wt-%, respectively, of the liquid initially present in the material had been removed.

Figure 8:
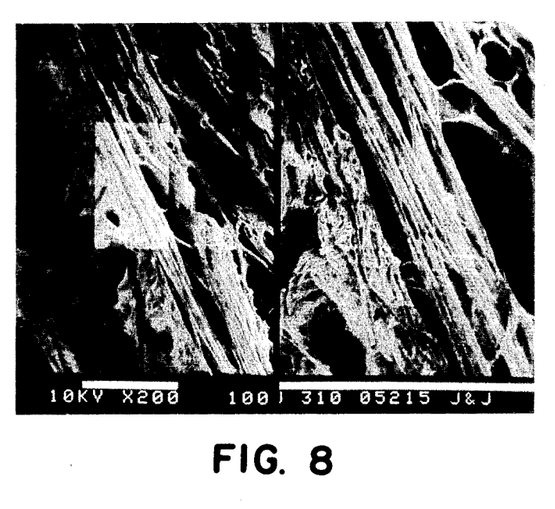
FIG. 8 is a photomicrograph at 200× and 800× magnifications of a cross-section from an *A. xylinum* pellicle derived from the same species as in FIG. 1, pressed to about 91 wt-% liquid removal, thereafter boiled in an aqueous 2 wt-% sodium hydroxide solution for three one-hour periods with pressing after each boiling period, repeated washing and pressing after the boiling periods, finally pressed to a 98 wt-% liquid removal, and then re-expanded by immersion in water.
Figure 16:
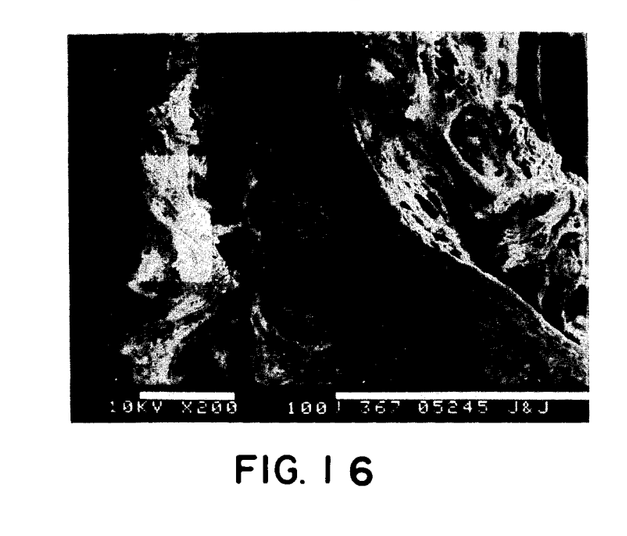
FIG. 16 is a photomicrograph at 200× and 800× magnifications of a cross-section of a pellicle derived from the same species as in FIG. 9, treated in the same manner as the pellicle of FIG. 8 except first pressed to about 85 wt-% liquid removal and finally to about 95 wt-% liquid removal.

The materials shown in FIGS. 8 and 16 were processed in the same manner as the materials shown in FIGS. 7 and 15 and were then immersed in water at 4° C. for twenty-four hours prior to storage at 4° C.

EXAMPLE 2

Testing of Physical Properties

Tensile Strength

Average force required to break the sample was determined using 1"×5" samples tested at a 2" jaw gap in non-slipping, non-cutting, cylindrical clamps. The testing was done on a calibrated Instron unit at a jaw separation rate of five centimeters per minute. The results are summarized in Table I, below.

TABLE I

| | Tensile Strength Summary | |
|---|---|---|
| Sample | Tensile Strength, g[1] | Relative Tensile[2] |
| FIG. 1 | 2,400 | 1.00 |
| FIG. 2 | 4,450 | 1.85 |
| FIG. 3 | 2,170 | 0.91 |
| FIG. 4 | 2,480 | 1.03 |
| FIG. 5 | 3,420 | 1.43 |
| FIG. 6 | 2,700 | 1.13 |
| FIG. 7 | 4,460 | 1.86 |
| FIG. 8 | 2,860 | 1.19 |

TABLE I-continued

Tensile Strength Summary

| Sample | Tensile Strength, g[1] | Relative Tensile[2] |
|---|---|---|
| FIG. 9 | 5,670 | 1.00 |
| FIG. 10 | 10,000 | 1.80 |
| FIG. 11 | 5,450 | 0.98 |
| FIG. 12 | 6,650 | 1.20 |
| FIG. 13 | 8,250 | 1.48 |
| FIG. 14 | 6,080 | 1.09 |
| FIG. 15 | 7,760 | 1.39 |
| FIG. 16 | 5,430 | 0.98 |

[1] Values are averages of six separate tests.
[2] Relative values are for samples of FIG. 1 through FIG. 8 and FIG. 9 through FIG. 16; the two groups are not compared since the two strains of *A. xylinum* did not produce microbial cellulose pellicles of equivalent basis weight.

The tensile strength values shown in Table I indicate that pressing of an otherwise unprocessed microbial cellulose pellicle enhances its tensile strength. For example, pressing to 98 wt-% liquid removal (FIG. 2) resulted in an increase in tensile strength by about 85% as compared to the unprocessed standard (FIG. 1). Similarly, the tensile strength of a pellicle from the other strain of *A. xylinum* pressed to a 95 wt-% liquid removal (FIG. 10) increased its tensile strength by about 80% as compared to the unprocessed standard (FIG. 9).

These tensile strength values also show that when the pressed pellicles were immersed in water for 24 hours, the tensile strength thereof returned to that of an unpressed pellicle even though structural modifications effected by pressing were retained.

The multiple pressing steps appear to enhance tensile strength as well. For example, comparing the values for FIGS. 7 and 1 it can be seen that pressing to 91 wt-% liquid removal followed by pressing to 98 wt-% liquid removal elevated the tensile strength by about 86% as compared to the unpressed pellicle. Similarly, comparing FIGS. 15 and 9 it can be seen that multiple pressing steps elevated the tensile strength by 39%.

Peel Strength

Average force required to peel the sample at mid-plane was determined using $\frac{1}{2}'' \times 3''$ samples tested at a 1'' jaw gap on a calibrated Instron unit. Samples were slit at mid-plane and opposing surfaces were pulled apart at a rate of five centimeters per minutre.

This test was intended to determine whether the various processing techniques differentially affected fiber interaction at the core of the microbial cellulose material. The test data are summarized in Table II, below.

TABLE II

Mid-Plane Peel Strength

| Sample | Peel Strength, g[1] | Relative Peel Strength[2] |
|---|---|---|
| FIG. 1 | 8.3 | 1.00 |
| FIG. 2 | 36.8 | 4.43 |
| FIG. 3 | 13.3 | 1.60 |
| FIG. 4 | 21.0 | 2.53 |
| FIG. 5 | 66.4 | 8.00 |
| FIG. 6 | 16.0 | 1.93 |
| FIG. 7 | 18.9 | 2.28 |
| FIG. 8 | 27.1 | 3.25 |
| FIG. 9 | 29.2 | 1.00 |
| FIG. 10 | 85.4 | 2.92 |
| FIG. 11 | 50.1 | 1.72 |
| FIG. 12 | 83.1 | 2.85 |
| FIG. 13 | 127.0 | 4.35 |
| FIG. 14 | 74.3 | 2.54 |
| FIG. 15 | 114.0 | 3.90 |
| FIG. 16 | 68.1 | 2.33 |

[1] Values are averages of five tests.
[2] Relative values are not compared between FIGS. 1-8 and FIGS. 9-16 since the morphology of the pellicles from the two strains of *A. xylinum* was different.

The peel strength values shown in Table II, above, indicate that the pressing of the microbial cellulose pellicles increases peel strength and that subsequent immersion of pressed pellicles in water reduces the peel strength somewhat as compared to pressed pellicles. However, the peel strength of pressed and immersed pellicles remains higher than the peel strength of unpressed pellicles.

Penetration Force

Average forces required for a pointed metal probe to penetrate a sample in a direction perpendicular to the x-y plane (Z-force; flat sample plane) and in a direction parallel with the x-y plane (X,Y-force) were determined using $1'' \times 4''$ samples. Testing was done on a calibrated Instron unit with the probe being driven into the sample at a rate of 25 centimeters per minute. The test results are summarized in Table III, below.

TABLE III

Z- and X,Y-Penetration Forces

| Sample | Z-Force, g[1] | Relative Z-Force[2] | X,Y-Force, g[3] | Relative X,Y-Force[2] |
|---|---|---|---|---|
| FIG. 1 | 88.5 | 1.00 | 198 | 1.00 |
| FIG. 2 | 113.0 | 1.28 | 465 | 2.35 |
| FIG. 3 | 128.0 | 1.45 | 327 | 1.65 |
| FIG. 4 | 55.0 | 0.62 | 188 | 0.95 |
| FIG. 7 | 78.4 | 0.89 | 470 | 2.37 |
| FIG. 8 | 75.7 | 0.86 | 342 | 1.73 |
| FIG. 9 | 114 | 1.00 | 404 | 1.00 |
| FIG. 10 | 92.9 | 0.82 | 950 | 2.35 |
| FIG. 11 | 114 | 1.00 | 380 | 0.94 |
| FIG. 12 | 77.7 | 0.68 | 337 | 0.83 |
| FIG. 15 | 111 | 0.97 | 1,048 | 2.59 |
| FIG. 16 | 128 | 1.12 | 349 | 0.86 |

[1] Values are averages of at least five tests.
[2] Relative values are for FIGS. 1-4 and FIGS. 7 and 8 and separately for FIGS. 9-12 and FIGS. 15 and 16 due to different basis weights and to different morphology.
[3] X,Y-force is the force required to penetrate the edge of the structure while Z-force is the force required to penetrate the structure in a direction perpendicular to its planar surfaces.

The data reported in Table III, above, indicate that the force required to penetrate the microbial cellulose structure in a direction perpendicular to the general plane of the pellicle as grown did not change greatly with processing variations. On the other hand, the force required for edge penetration did vary widely depending upon the processing conditions.

Edge Tear Force

Average force required to propagate a tear in a microbial cellulose structure from the center of the structure to one edge of the structure was determined using $1'' \times 3''$ sampales. The tear was initiated by a relatively stiff pull-wire that was passed through each sample at about the longitudinal axis of the sample and spaced about one inch from one end (the free end) of the sample. The pull-wire was held in one jaw of a calibrated Instron unit and the other end (the captured end) of the sample was held in the other jaw of the Instron unit. The sample was then pulled against the pull-wire in the Instron unit at a jaw separation rate of five centimeters per minute. The test data are summarized in Table IV, below.

TABLE IV

| Sample | Force for Edge Tear Force, g[1] | Relative Force[2] |
|---|---|---|
| FIG. 1 | 172 | 1.00 |
| FIG. 2 | 93.0 | 0.54 |
| FIG. 3 | 131 | 0.76 |
| FIG. 4 | 114 | 0.66 |
| FIG. 7 | 98.3 | 0.57 |
| FIG. 8 | 148 | 0.86 |
| FIG. 9 | 241 | 1.00 |
| FIG. 10 | 208 | 0.86 |
| FIG. 11 | 247 | 1.02 |
| FIG. 12 | 318 | 1.32 |
| FIG. 15 | 221 | .92 |
| FIG. 16 | 242 | 1.00 |

[1]Values are averages of three tests.
[2]Relative values of FIGS. 1-4, 7 and 8 and FIGS. 9-12, 15 and 16 are not compared for reasons stated above.

Relative Tensile Strength

Average tensile strength values were calculated for a series of samples in increments of 5% extension based on original sample length. These calculations are compiled in Table V, below.

TABLE V

| Sample Processed As In | Relative Tensile Strength in Grams per 5% Increment Extension[1] Extension | | | | | | | | |
|---|---|---|---|---|---|---|---|---|---|
| | 5% | 10% | 15% | 20% | 25% | 30% | 35% | 40% | 45% |
| FIG. 1 | 119 | 278 | 560 | 915 | 1,320 | | | | |
| FIG. 1 | 1.0 | 1.0 | 1.0 | 1.0 | 1.0 | | | | |
| FIG. 2 | 4.87 | 3.97 | 2.86 | 2.32 | 2.16 | | | | |
| FIG. 3 | 0.82 | 0.77 | 0.78 | 0.82 | 0.87 | | | | |
| FIG. 4 | 0.95 | 0.95 | 0.91 | 0.92 | 0.92 | | | | |
| FIG. 5 | 1.96 | 1.70 | 1.38 | 1.25 | 1.18 | | | | |
| FIG. 7 | 4.20 | 3.72 | 2.76 | 2.30 | 2.01 | | | | |
| FIG. 8 | 1.15 | 1.08 | 1.04 | 1.04 | 1.06 | | | | |
| FIG. 9 | 120 | 233 | 313 | 493 | 747 | 1,117 | 1,607 | 2,267 | 3,110 |
| FIG. 9 | 1.0 | 1.0 | 1.0 | 1.0 | 1.0 | 1.0 | 1.0 | 1.0 | 1.0 |
| FIG. 10 | 4.83 | 4.72 | 5.10 | 4.35 | 3.73 | 3.17 | 2.72 | 2.32 | 1.88 |
| FIG. 11 | 1.48 | 1.38 | 1.43 | 1.27 | 1.12 | 1.00 | 0.93 | 0.81 | 0.81 |
| FIG. 12 | 0.81 | 0.56 | 0.68 | 0.69 | 0.72 | 0.76 | 0.79 | 0.80 | 0.85 |
| FIG. 13 | 2.92 | 2.93 | 3.55 | 3.50 | 3.32 | 3.10 | 2.78 | — | — |
| FIG. 15 | 5.44 | 5.72 | 6.39 | 5.69 | 5.06 | 4.35 | 3.72 | 3.15 | 2.60 |
| FIG. 16 | 0.92 | 0.89 | 1.18 | 1.25 | 1.24 | 1.19 | 1.17 | 1.16 | 1.14 |

[1]Extension was measured in 5% increments based on original sample length; zero point was taken to be at the 50-gram tensile load level.
[2]This line gives absolute tensile values in grams.
[3]Normalized values are reported in vertical columns in order to give relative tensile values per processing type.

The data in Table V, above, indicate that the highly pressed materials are much stiffer than the samples that were not pressed. It is also seen that the sodium hydroxide treatment weakens the pressed structure as well as the unpressed structure, and that the higher the water content of the pressed samples the lower is the tensile strength at a given extension. The data also indicate a rapid decrease in the relative tensile strength value compared to the unprocessed specimens. This is believed to be due to the thickness reduction in the unpressed material under tensioning which results in expression of liquid from the specimen.

Fluid Absorption

Absorption of water by pellicles pressed to different degrees of water removal was determined by immersing pellicle portions into water for a predetermined time period and thereafter weighing these portions. The observed data are reported in Table VI, below.

TABLE VI

| | Liquid Absorption by Pressed Pellicles[1] Increase in Sample Weight, %[2] | | |
|---|---|---|---|
| Time, sec. | 91 wt % Pellicle[3] | 30 wt % Pellicle[4] | Difference |
| 10 | 9.6 | 3.1 | 6.5 |
| 30 | 11.3 | 4.9 | 6.4 |
| 60 | 15.0 | 9.5 | 5.5 |
| 300 | 20.9 | 14.5 | 6.4 |
| 900 | 24.3 | 19.2 | 5.1 |
| 3600 | 26.6 | 25.7 | 0.9 |

[1]Samples of same pellicle were pressed to 91 wt % and 30 wt % liquid removal.
[2]Values listed as percent of original sample weight (which was the same for both columns of data).
[3]Pellicle from which 91 wt % of original liquid was removed.
[4]Pellicle from which 30 wt % of original liquid was removed.

The data in Table VI inddicate that the pressed material at 91 wt-% liquid removal level reabsorbed water more rapidly than the same material pressed to the 30 wt-% liquid removal level. The above data have also been confirmed by dye penetration studies which showed a more rapid dye uptake by pellicles pressed to a higher water removal level. Thus, a more rapid and more uniform loading of pressed microbial cellulose pellicles with liquid monomers, liquid polymers, liquid medicaments and other working fluids can also be effected as long as such fluids wet the produced laminar structure.

Visual examination by scanning electron microscope of microbial cellulose pellicles treated in accordance with the present invention reveals morphological changes in the structure as compared to the natural pellicle. These changes can be characterized as a transformation of the naturally occurring fibrous network into a layered structure having interconnected, densified lamellae that border or circumscribe zones of relatively low fibril density. The physical test data reported above substantiate the visual observations that gradual pressing of the pellicle to express the major portion of liquid contained therein permanently alters the structure as well.

EXAMPLE 3

Production of Cellulosic Laminar Structure from a Microbial Cellulose Pellicle A sterile culture tray (50×50×10 cm) was filled with sterile culture medium to a depth of about 1.5 cm, inoculated with 95 cc of an inoculum having a bacterial concentration of about $10^8$ *A. xylinum* per cc, covered and placed in a culture room at 20° C. where it remained undisturbed for 9 days. At the end of the culture period, a fibrous gel-like pellicle of bacterial cellulose had formed to a thickness of about 1.5 centimeters. The pellicle, as removed from the tray, was determined to contain about 10 grams cellulose and 1500 grams nutrient liquid. The pellicle was gently pressed between absorbent sheets to expel about 80 percent by weight of the liquid content thereof and then treated with NaOH to remove entrapped bacteria cells and cell debris.

To that end, the obtained pressed mat, having a laminar structure, was transferred to an aqueous NaOH solution (about 3% by wt NaOH) and soaked for therein for 12 hours. During the soaking time the mat reabsorbed about 70 percent by weight of the original liquid content of the pellicle. While immersed in the NaOH solution, the mat was again pressed to expel about 80 percent by weight of its liquid content and again soaked to reabsorb the NaOH solution. This procedure was repeated a third time. Thereafter the pressed mat was removed from the NaOH solution, pressed between absorbent sheets and transferred to an aqueous, hydrochloric acid solution (about 3% by weight) to neutralize the NaOH present. The pressed mat was soaked in acid solution, then pressed between absorbent sheets and transferred to a bath of distilled water. The obtained, neutralized mat was repeatedly pressed and allowed to reabsorb in fresh, distilled water until substantially all of the sodium chloride salt was removed and the pH of the rinse water was observed to be neutral.

The washed, neutralized, and water-loaded mat was about 0.9 centimeters thick. That is, the mat had about 60% of the thickness of the pellicle and possessed excellent strength, handling and drape characteristics. The cellulose content of the water-loaded mat was determined to be about 40 $g/M^2$ and the water content about 3600 $g/M^2$. The mat was sterilizable by autoclaving or cobalt-60 radiation and, after sterilization, was suitable for use as a sterile wet dressing for wounds or burns.

Liquid loaded dressings of the present invention control local wound environment, particularly moisture content, are substantially lint-free, and provide the benefits of gel dressings in a system free of potential chemical irritants such as unreacted monomers. The liquid holding capacity of the dressings of the present invention on a weight basis is far greatear than that of a conventional gauze dressing.

EXAMPLE 4

Liquid-Containing Laminar Sheet Made From Microbial Cellulose

A water-loaded laminar structure prepared according to Example 3 was hand-pressed between absorbent sheets to reduce the water content of the mat to about 320 $g/M^2$. Thereafter the resulting laminar web was deformed by compressing the web into a thin, strong, wet, membrane-like sheet. The resulting, membrane-like sheet was observed to have a thickness of less than about 1 mm. The weight ratio of water to cellulose in the sheet was approximately 8:1. Sheets having a weight ratio of water to cellulose in the range of from about 2:1 to 20:1 may be prepared in a similar manner. The compressed sheet material is suitable for use as a protective wound covering or as a surgical wipe. When applied to wounds and covered with an occlusive backing film, such sheet materials have a capacity to absorb large quantities of wound exudate.

EXAMPLE 5

Liquid-Containing Dressing

Compressed membrane-like sheets prepared according to Example 4 were immersed in water, water/glycerine or saline. Upon immersion they recovered about 70% by weight of their original liquid content and thickness. When placed on a skin surface, these dressings demonstrated a cooling effect due to evaporation of the liquid and were found to be suitable for use as burn dressings. The obtained sheet material, reloaded with liquid, was also suitable for use as a tissue/organ drape to prevent drying of exposed organs or tissue during extended surgical procedures.

EXAMPLE 6

Lint-Free Dressing

The method of Example 4 was repeated except the membrane-like sheet material was immersed in glycerol in one case and in polyethylene glycol (MW 400) in a second case. The resulting sheet-form product in each case contained about 2000 $g/M^2$ liquid, was strong and flexible, exhibited good hand and drape, and did not dry out when exposed to air. The sheet-form material was transparent to an extent permitting visual examination of skin condition through the material when it was applied to the skin. The material was substantially lint-free and was suitable for use as a general purpose dressing.

EXAMPLE 7

Wound Covering

A water-loaded laminar web prepared according to Example 3 was air-dried to a thin, flexible sheet. The dried sheet was then immersed in glycerol and was observed to regain about 5 percent by weight of its original liquid content. The resulting material was thin, strong and suitable for use as a wound covering.

EXAMPLE 8

Burn Dressing Containing a Gel

The method of Example 4 was repeated except the obtained membrane-like sheet material was immersed into an aqueous solution of polyvinylpyrrolidone (10% by weight PVP). After the membrane had recovered about 70 percent by weight of its original liquid content, the sheet material was removed from the PVP solution, weighed, and air-dried to about 50% of its weight after removal from the PVP solution. The concentration of PVP retained within the sheet material was thereby increased to about 20 percent by weight of the liquid content. The concentrated PVP solution-containing sheet material was thereupon exposed to electron beam radiation at a dose of 2.5 megarads to crosslink the PVP solution and form a gel within the cellulosic framework of the sheet material. The resulting product was strong and flexible, and suitable for use as a wound or burn dressing. Similar results are obtained by substituting other water soluble, crosslinkable polymers or monomers for the PVP, such as, for example, polyethylene oxide or sodium acrylate.

EXAMPLE 9

Burn Dressing Containing an Ointment method of Example 4 was repeated except the membrane-like sheet was treated with silver sulfadiazine (SSD) ointment (1% by weight SSD in a water-miscible emulsion). The compressed sheet material was immersed in SSD ointment which had been warmed to fluid state until the ointment content of the pellicle had increased to about 1000 g/M$^2$. The impregnation with SSD ointment was conducted in a dark room and the resulting sheet-form product, suitable for use as a burn dressing, was packaged in a light proof, moisture-impervious aluminum foil packet. A similar product is obtained by impregnating the membrane-like sheet material with an aqueous solution of zinc sulfadiazine. In another embodiment, the membrane-like sheet may be surface-coated with silver sulfadiazine powder so that the antiseptic is applied directly to the burn site.

EXAMPLE 10

Petrolatum-Coated Dressing With Aqueous Core

The method of Example 4 was repeated except the membrane-like sheet material was immersed in water until a water loading of about 2000 g/M$^2$ was attained. The water-loaded sheet material was thereafter immersed in melted petrolatum bath at a temperature of 100° C. for 1 hour, removed from the bath and allowed to drain. The resulting product was a petrolatum-coated dressing having a water core. This dressing had a reduced tendency to adhere to wounds.

EXAMPLE 11

Apertured Laminar Structure Derived From Microbial Cellulose

A water-loaded pellicle was grown and treated as in Example 3, except that the lid of the culture tray was provided with downward projecting cylindrical rods attached in a square pattern. The rods were ⅛ inch in diameter and were set at the corners of a ⅜ inch square pattern. The free end of each rod extended downwardly and in a direction substantially perpendicular to the lid for a sufficient distance so that when the culture tray was loaded with medium and the lid put in place, the rods penetrated the surface of the medium. The pellicle produced in such an apparatus was perforated with holes corresponding to the pattern of the rods. Further treatment of the obtained perforated mat as in Examples 4 and 10 resulted in a structure which, when used as a primary dressing on exudating wounds, allowed transport and removal of exuded body fluid through the holes and into an absorbent secondary dressing placed over the primary dressing.

Each of the above examples illustrates the preparation of a liquid-loaded laminar structure from a pellicle of microbially-produced cellulose wherein the fibrous structure of the pellicle has been modified, and wherein the nutrient medium and cells inherently entrapped in the pellicle during its formation have been replaced with a physiologically-acceptable liquid. The weight ratio of liquid to cellulose in such pellicle is typically from about 5:1 to 100:1, and in some circumstances may be 150:1 or higher. The physiologically acceptable liquid may be distilled water, saline, glycerol, polyethylene glycol, isopropanol or other lower alcohols, petrolatum, mixtures thereof, or any other physiologically acceptable material. In each case, the liquid loaded pad is sterilized prior to use in a medical application using conventional, appropriate means such as autoclaving or radiation.

The NaOH treatment described in Example 3 for removal of entrapped bacteria cells and cell residues or debris from the pellicle may be modified or replaced with equivalent results. For example, the pellicle may be boiled in a 1 to 10 percent by weight solution of NaOH or KOH for up to 1 hour or more to effectively remove the bacteria, then neutralized with hydrochloric, acetic, or other suitable acid and washed with distilled water as described. Alternatively, the bacteria may be removed from the pellicle by treatment with other agents such as trichloroacetic acid, and the like, or rendered unreactive by crosslinking with gluteraldehyde, formaldehyde, or dialdehyde starch.

While for some appllications the presence of bacteria cells and/or cell debris is not objectionable, removal of entrapped bacterial cells and debris is desirable when preparing materials for surgical uses, particularly for use as moist tissue/organ drapes. The untreated pellicle is likely to contain endotoxins resulting from the rupture of the bacteria cells which, if absorbed by a living organism in sufficient quantities, would cause a pyrogenic reaction. In the mats or laminar structures derived from *A. xylinum* the concentration of lipopolysaccharide endotoxins in the final, neutralized and washed material prepared according to Example 3 is about 1 to 50 nanograms per gram of material. By contrast, the endotoxin content of a pellicle which has been mechanically worked to rupture the *A. xylinum* cells, but not chemically treated, may be 10,000 nanograms per gram of material or higher.

In pyrogen-sensitive applications, care must be taken to assure not only that the bacterial endotoxins are removed during processing, but that the obtained material is subsequently handled under pyrogen-free conditions and is loaded only with substantially pyrogen-free substances.

The treatment to remove entrapped bacteria is optional in preparing certain products of the present invention where no harmful consequences result if this step is omitted, as for example, in the preparation of skin wipes or surface dressings, since the bacteria would, of course, be killed along with any other pathogenic microorganisms which might be present when the produced material is sterilized as required for medical use.

EXAMPLE 12

Evaluation of a Wound Dressing

The glycerol-loaded material of Example 6 was sterilized in a steam autoclave and evaluated as a wound dressing in animal studies involving full thickness dorsal incision in guinea pigs. The dorsal area of a guinea pig was shaved and a full thickness section of skin about 2.5 centimeters in diameter was surgically removed. A dressing was applied and the extent of wound contraction after 8 days was determined. In the case of the material of Example 6, wound contraction after 8 days was about 50% which was equivalent to that generally obtained with currently available occlusive surgical dressings.

Due to the permeability and biological inertness of the materials of this invention, these materials are particularly suited for the incorporation therein of a wide variety of chemotherapeutic agents, medicinal agents and additives. For instance, the dressings can contain topical anesthetics such as butamben picrate, lidocaine hydrochloride, piperocaine hydrochloride and the like; bacteriostatic agents such as silver nitrate (0.5% by weight solution), sulfa drugs, for example 10% by weight suspension of p-aminomethylbenzene sulfonamide in a water dispersible cream, benzalkonium chloride and the like; antibiotics such as bacitracin, neomycin, aureomycin, tetracycline, penicillin, polymyxin streptomycin, signemycin, erthromycin, oleandomycin, and the like; topical steroids such as prednisone, dexamethasone, hydrocortisone and the like; enzymes such as collagenase, fibrinolysine, desoxyribonuclease and the like; coagulants and anticoagulants; antifungal agents, such as isopropanol, nystatin, miconazole, ketoconazole, tolnaftate and the like. Nonwater soluble medicaments such as silver sulfadiazine are preferably dispersed in nonaqueous ointment bases which may be liquified to impregnate the pellicle as hereinbefore described.

The quantity of the aforementioned medicinal agents, chemotherapeutic agents or additives which can be incorporated into the liquid loaded materials will, of course, be dependent upon the particular agent, its solubility, and the presence of other additives. In general, however, the agents will be employed in a therapeutic amount. This can range from about 0.0001 percent by weight and lower, upwards to about 40 percent by weight and higher. A unique feature of the present materials is that additional or different chemotherapeutic agents or medicaments can be added to the dressing while in place and transported to the site of the wound by diffusion through the material. Hence, it is possible either by incorporating medicaments directly into the material before use, or by applying medicaments to the material while in place over the injured area, to provide a controlled supply of medication to the wound site. As a result of the high liquid-holding capacity of the products of the present invention, materials loaded with a medicament carry a greater amount of the active agent to the treatment site per gram of dressing than comparable conventional dressings.

The liquid loaded laminar structures of the present invention are substantially lint-free and may be used with good results as skin and surgical wipes. Because the materials contain a high liquid content, a wipe of a given size contains a greater amount of available liquid than, for example, a wetted gauze sponge, and may effectively wipe a greater area with no deposition of lint or gauze fragments. Pads to be used as wipes are preferably loaded with isopropanol. Liquid release from wipes prepared in accordance with the present invention effects liquid delivery to a wiped surface in a semi-controlled manner. That is, liquid delivery over a relatively large number of wiping cycles (about 20 to 30 cycles) is more nearly constant than that for standard wipes such as paper towels, woven gauze, spun-laced non-woven fabrics, and the like.

The liquid loaded laminar materials of the present invention may be used as wet dressings in combination with an occlusive film backing for some applications. For example, in the case of an ulcer dressing which is required to provide a wound environment conducive to the growth of new tissue, the dressing should provide a source of moisture over an extended period of time and ensure an antibacterial environment. A dressing of the present invention loaded with an aqueous solution containing an antimicrobial agent may be applied to such an ulcer and covered with an occlusive film backing to prevent evaporation of moisture from the dressing. A wide variety of films are suitable for use as backings for a wound dressing including, for example, polyvinylidene chloride, polyethylene, polypropylene, polyethylene terephthalate, polyamides, polyvinyl chloride, cellulose acetate and derivatives thereof, polydimethyl butadiene, polyurethanes, polyvinyl alcohol, silicone rubbers, polyacrylic acid, and the like. The film may be attached to the liquid loaded material by the surface tension of the liquid or through the use of adhesives or mechanical fastening if preferred. In one embodiment of the invention, the backing film may extend beyond the area of the dressing and be adhesive coated to form an island dressing which may be secured directly to the skin of the patient.

Liquid loaded materials intended specifically for use as burn dressing should provide for evaporation from the dressing to provide a cooling effect over the wound area. Such dressings are accordingly loaded with an evaporative liquid which may be water, saline or a water/glycerol or water/polyethylene glycol solution and are not covered with an occlusive backing film during use. The products of this invention may also be produced in long lengths for use as burn bandages, and in large sheets, i.e., 3 by 5 feet or greater, for use as burn blankets.

Cold packs for burns, as distinguished from burn dressings may be provided with a removable insulating backing since cold packs are chilled prior to application and do not initially depend upon evaporative cooling. The cooling effect of the cold pack may be extended by removing the backing and allowing evaporative cooling to take place after the initial cooling capacity due to thermal differential has been exhausted. Cold packs additionally may utilize thicker or multiple layers of liquid loaded material to increase their heat capacity.

Liquid loaded materials according to the present invention also may be used as long-term coverings for severe burns and certain other wounds. For this particular application, a thin dressing embodying this invention, about 0.1 to about 5 millimeters thick, is placed immediately over the wound and a second dressing embodying this invention and containing medicaments or other wound treating agents is placed over the primary dressing. Since the medicaments will migrate through the primary dressing to the wound surface, the secondary dressing may be changed from time to time to renew the medicament treatment while the healing process of the wound is observed through the primary dressing which is not disturbed.

While the products of the present invention inherently have high strength, various reinforcing materials such as random or carded fibers, plastic net, reticulated plastic film, open weave fabrics, scrims and/or fabric mesh may be incorporated in the dressing structure if desired. For example, nylon gauze, rayon net, polyester (e.g., "Dacron") or cellulose mesh or reticulated polyethylene can be embedded in the pellicle while the pellicle is being formed. For example, the reinforcing material can be placed carefully on the surface of the nutrient medium of an active culture containing a relatively thin pellicle of bacterial cellulose, with care being taken not to break the surface tension of the nutrient medium. As the production of cellulose continues, the reinforcing material is encapsulated by newly formed cellulose and carried down into the nutrient medium as new cellulose is produced at the surface of the nutrient medium.

An additional feature of the wet dressings of the present invention is their ability to absorb large quantities of fluid from the wound site when the dressing is applied in a less than saturated condition. In the case of burn dressings, moisture evaporating from the dressing will tend to be replaced by fluids exuding from the burn site. In other cases, a dressing which has been compressed to expel its normal liquid content or which has been partially predried may be used directly to absorb wound exudate. Preferably, such a dressing is covered with an occlusive film to prevent the dressing from drying out while in place over the wound.

When a dressing of this invention is allowed to dry while in place over a wound or burn site, the dressing adheres to the wound and upon removal, provides a degree of debridement which assists in cleansing the wound site. When it is desirable to avoid adherence, the dressing should be removed before drying, or should be loaded with a nonadherent material such as petrolatum as described in Example 10.

The liquid loaded materials of the present invention are sterilized prior to use by any appropriate method such as autoclaving or irradiation with cobalt-60 or electron beam. The materials are packaged in sterile hermetically sealed moisture-proof containers. Most preferably, the materials are heat sealed in packages constructed of aluminum foil laminated with a heat sealable polymeric film such as polyethylene, and sterilized in the package by irradiation in accordance with conventional methods for packaging surgical products. Sterile materials may be stored for extended periods of time with no adverse effect.

As is apparent from the preceding description and examples, a wide variety of products may be produced from the fibrous materials of the present invention derived from microbially-produced polysaccharides such as microbial cellulose. These products may be formed in a variety of shapes, sizes, and thicknesses, and may be loaded with a variety of physiologically-acceptable liquids and medicaments to accommodate the requirements of any particular application. Additionally, the fibrous materials may be used in combination with internal reinforcements or external backing films and may be used as the pad portion of island dressings which include adhesive attachment means. Many other variations and the details of construction and composition will be apparent to those skilled in the art and such variations are contemplated within the broad scope of the present invention.

We claim:

1. A self-supporting, laminar polysaccharide structure constituted by (a) densified, interconnected laminae that merge into one another and define channels therebetween and (b) polysaccharide microfibrils situated within the defined channels and connected to the laminae.

2. The laminar structure in accordance with claim 1 wherein the polysaccharide is microbial cellulose.

3. The laminar structure in accordance with claim 1 having a water content of up to about 100 times the weight of the polysaccharide constituting the structure.

4. The laminar structure in accordance with claim 1 and substantially free from cells and cell debris.

5. The laminar structure in accordance with claim 1 and substantially pyrogen free.

6. The laminar structure in accordance with claim 1 and containing no more than about 0.1 percent by weight of protein, based on the weight of the polysaccharide constituting the structure.

7. The laminar structure in accordance with claim 1 and containing no more than about 1 percent by weight of ash, based on the weight of the polysaccharide.

8. The laminar structure in accordance with claim 1 and containing no more than about 0.001 percent by weight of heavy metal ions, based on the weight of the polysaccharide.

9. The laminar structure in accordance with claim 1 and containing no more than about 0.00001 percent by weight of endotoxins, based on the weight of the polysaccharide.

10. The laminar structure in accordance with claim 1 further containing water and a water-miscible, organic liquid fiber lubricant having a vapor pressure at 25° C. no more than that of water; said lubricant being present in a polysaccharide-to-lubricant weight ratio of about 100 to about 0.007.

11. The laminar structure in accordance with claim 10 wherein the lubricant is a polyhydric aliphatic alcohol.

12. The laminar structure in accordance with claim 10 wherein the lubricant is a sugar alcohol.

13. The laminar structure in accordance with claim 10 wherein the lubricant is a liquid polyethylene glycol of the formula $$H(OCH_2CH_2)_nOH$$

wherein n is an integer having a value of at least 4.

14. A pliant, water-absorbent, laminar mass of microbial cellulose, partially saturated with water and containing a liquid polyhydric alcohol in a cellulose-to-alcohol weight ratio of about 100 to about 0.007; the amount of water present being in the range of about 10,000 to about 30 percent by weight, based on the weight of microbial cellulose present.

15. The pliant laminar mass in accordance with claim 14 wherein the polyhydric alcohol is glycerol.

16. The pliant laminar mass in accordance with claim 14 wherein the polyhydric alcohol is sorbitol.

17. The pliant laminar mass in accordance with claim 14 wherein the polyhydric alcohol is ethylene glycol.

18. The pliant laminar mass in accordance with claim 14 wherein the polyhydric alcohol is propylene glycol.

19. A method for producing a self-supporting laminar polysaccharide structure structure which comprises the steps of
providing a water-containing microbial polysaccharide pellicle;
pressing said pellicle by laterally applied pressure to a thickness of no more than about 25 percent of the original thickness thereof so as to express at least some of the water contained therein and to effect a permanent rearrangement into lamellae of at least some of the polysaccharide strands constituting said pellicle; and
thereafter releasing the laterally applied pressure on the pellicle.

20. The method in accordance with claim 19 wherein the microbial polysaccharide pellicle is a microbial cellulose pellicle.

21. The method in accordance with claim 19 wherein the microbial polysaccharide pellicle is an *Acetobacter xylinum* pellicle.

22. A method for producing a water-absorbent article from a water-containing fibrous mass of microbial cellulose which comprises the steps of providing a laminar mass of microbial cellulose partially saturated with water; and introducing into the microbial cellulose mass a water-miscible, organic liquid fiber lubricant having a vapor pressure of no more than 24 mm Hg at 25° C. in a cellulose-to-lubricant weight ratio of about 100 to about 0.007.

23. The method in accordance with claim 22 including the further step of removing at least some of the water present in the fibrous mass after the lubricant has been introduced therein.

* * * * *